United States Patent [19]
Ladtkow et al.

[11] Patent Number: 5,541,376
[45] Date of Patent: Jul. 30, 1996

[54] SWITCH AND CONNECTOR

[75] Inventors: James R. Ladtkow, Thornton; Glenn A. Horner, Boulder, both of Colo.; Richard W. Petersen, Hackettstown, N.J.

[73] Assignee: Valleylab Inc, Boulder, Colo.

[21] Appl. No.: 218,786

[22] Filed: Mar. 28, 1994

[51] Int. Cl.$^6$ ............................................ H01H 1/00
[52] U.S. Cl. ............................ 200/284; 200/409; 439/404
[58] Field of Search ............................... 200/284, 302.1, 200/302.2, 409, 406, 51.05; 439/404, 417, 719

[56] References Cited

U.S. PATENT DOCUMENTS

| | | |
|---|---|---|
| D. 287,879 | 1/1987 | Braxton et al. |
| 3,801,766 | 4/1974 | Morrison, Jr. et al. |
| 4,256,358 | 3/1981 | Genz ................................ 200/284 X |
| 4,357,510 | 11/1982 | Fortuna ............................ 200/284 X |
| 4,624,049 | 11/1986 | Levko ............................... 200/284 X |
| 4,754,104 | 6/1988 | Maltais et al. .................... 200/284 X |
| 4,827,927 | 5/1989 | Newton . |
| 5,015,227 | 5/1991 | Broadwin et al. . |
| 5,147,215 | 9/1992 | Pritulsky ............................ 439/404 X |
| 5,277,616 | 1/1994 | Harting et al. .................... 439/417 |
| 5,295,857 | 3/1994 | Toly ................................. 439/417 X |

*Primary Examiner*—Renee S. Luebke
*Attorney, Agent, or Firm*—Peter C. Richardson; Lawrence C. Akers; Aaron Passman

[57] ABSTRACT

An insulating switch base with a top, bottom and an edge has openings through the top and one edge for a conductor. A conductive switch lead frame has proximal ends with insulation displacement connectors bent in the openings. A resilient member on the frame has a moveable contact and is conductively associated with a connector. A contoured arm on the frame is distal of, but conductive with, another connector. The arm is spaced from the resilient member as an open contact capable of momentary engagement. A frangible area on each frame is between the resilient member and the arm. Recesses in the top support retain the frame. A slot and barbs on each connector receive one conductor securely in an opening after aligned installation in an opening, seating of the frame in its recess and severing the area over a passage in the base. A membrane attaches over the frame and a molding is applied about the membrane leaving the resilient member open.

10 Claims, 4 Drawing Sheets

SWITCH AND CONNECTOR

FIELD OF THE INVENTION

A switch and the method of its automatic assembly and the tool therefor simplify the manufacture of a power control for an electrosurgical handpiece and more particularly, the high volume construction of a normally open switch.

BACKGROUND OF THE DISCLOSURE

Electrosurgical procedures performed with an electrosurgical generator and an electrosurgical pencil or handpiece require that the surgeon have control over the application of power directed to the human or animal patient. Specifically, the electrosurgical energy output of the electrosurgical generator can be set at the generator control panel which is remote from the sterile field of the operating site. It is also necessary that the application of the electrosurgical energy delivered to the handpiece be controlled, i.e. started and stopped as desired in the sterile field by the surgeon during the surgical procedure. Wherefore the surgeon has full control over the positioning of the handpiece and more particularly an electrosurgical electrode thereof and the initiation and completion of energy delivery.

Electrosurgical handpieces are common surgical instruments that need to be made in high volumes at relatively low costs. In addition the function of the handpiece must be reliable and safe. With regard to the former the delivery of electrosurgical energy as required should be consistent notwithstanding the demands of switching at high frequency, 500 kilocycles, and at high power up to three hundred watts. The switch mechanism is not only ergonomically oriented on the handpiece but also requires an indicative feel of on and off, a tactile manifestation of travel distance. The control must also be reliable and properly functional to indicate to the surgeon with the certainty that the control is operating as needed. In addition the switch has to prevent any misdirection or inadvertent application of electrosurgical energy to be safe.

Electrosurgery is the application of a radio frequency electrical energy to a surgical site on a human or animal patient for tissue cutting, coagulation, or a blend thereof. In monopolar mode the radio frequency energy that is generated by the electrosurgical generator is applied to tissue from an active electrode held in the handpiece by the surgeon, and is collected from a dispersive electrode attached to the patient. A small contact area of the active electrode causes a high current density so that a spark enters the tissue at the surgical site. This spark causes intense localized heating, eschar, fulguration and other effects, to achieve the cutting and/or coagulation. The dispersive electrode collects the energy returning it to the electrosurgical generator to complete an electrical circuit. The dispersive electrode is of a significant size so that the energy density collected thereby is low enough to avoid any surgical or heating effect that would burn.

A burn will develop if the power delivered to the tissue and after its passage through the body results in a high energy density at the exit so that localized tissue heating occurs. This situation happens when the energy is allowed to pass at a location other than the dispersive electrode such a condition is called leakage. A burn from leakage can be quite severe as the patient is anesthetized and will not react thereto. The burn area is frequently covered so the doctor or surgical attendants will not see it until it is too late to take corrective action.

Another potential path for leakage burns is to the surgeon through contact with the active electrode, the switch contacts, the conductors which supply the radio frequency, high voltage electrosurgical energy to the handpiece. Leakage in that circumstance may harm or burn the surgeon or one of the surgical attendants in contact with the switch contacts, the active electrode or its supply conductors and a ground. It is for this reason that leakage or alternate path energy flow in electrosurgery are of considerable concern and efforts are made to monitor and control leakage.

The early electrosurgical generators were of a ground referenced design. Being ground referenced, the return for the electrosurgical generator and the dispersive electrode were both connected to earth or ground. The ground referenced arrangement was satisfactory provided that no other point on the patient was grounded. When a monitoring electrode, i.e. EKG, was used during the electrosurgical procedure, and the monitoring electrode was referenced to ground, some portion of the electrosurgical energy could flow to ground through the monitoring electrode, instead of the preferred path back through the dispersive electrode. Since monitoring electrodes usually have small contact area, the current density at their contact may be sufficient to develop enough energy density to result in a burn. An even worse condition occurs if the electrosurgical generator connection to the dispersive electrode is accidentally separated. Thus, with no direct energy path back to the electrosurgical generator, all of the power travels through any alternate grounded paths, such as through the monitoring electrodes, the surgeon and/or the surgical table or perhaps through the handpiece switch. Severe burns are a possible result.

In an effort to reduce the risks associated with the ground referenced electrosurgical generators, the power output circuit of the electrosurgical generator was isolated from any other ground. Output isolated electrosurgical generators were a significant step in reducing the risks associated with alternate path burns, because the electrosurgical energy exiting the patient was more likely to flow through the dispersive electrode to complete the circuit and not through any other ground referenced points when returning to the electrosurgical generator. If the generator connection to the dispersive electrode became disconnected, a significant portion of the electrosurgical energy flow from the electrosurgical generator would stop.

Although isolated output electrosurgical generators was an improvement over the previous ground referenced units, a problem remained because the isolation from ground was not always perfect. At the relatively high frequencies of electrosurgical current, e.g., 500 kilohertz to 1 megahertz, stray capacitance to ground allows another ground referenced path. Furthermore, the amount of stray capacitance required to create this other significant path for ground referenced energy flow is not great. Although alternate paths of energy flow are less than those flowing if the electrosurgical generator was ground referenced, a potential exists for significant patient and alternate path burns. Consequently, adequate spacing of the switch contacts and insulation thereof is essential to safe operation.

Therefore the switch in the handpiece is frequently isolated so that switching the full energy delivered by the electrode is not across the contacts thereof. Various techniques including optocoupling, low power slave circuits and the like are used. Valleylab of Boulder, Colo., the assignee, of the present disclosure has manufactured and sold many handpieces of various styles and types and has several United States patents and applications including, 3,801,766; 4,827,927; 5,015,227; Des 287,879. Against this background and with an appreciation of the problem of accurately and automatically manufacturing a switch, further significant improvements and advancements in the control of electrosurgical energy, particularly during initiation and termination of electrosurgery, are required. Described herein are a method its tool and a product produced thereby not found in the literature or practiced in the field. The literature is of interest for its teachings of the knowledge of skilled artisans at the time of this invention.

SUMMARY OF THE INVENTION

A switch for an electrosurgical handpiece preferably has a plurality of contacts and a cable having a plurality of individually insulated separate electrical conductors each with a conductive core surrounded by a dielectric. An insulating switch base of a dielectric material is generally planar in shape. The insulating switch base may include a top and bottom larger than an edge surrounding thereabout. Configured openings may extend at least through the top of the insulating switch base and at least one edge thereof. The configured openings may each be ready to receive at least one of the insulated separate conductors.

A section within each configured opening might be located to redirect each insulated separate conductor when driven into to its respective configured openings to locate and support the insulated separate conductors within the insulating switch base after forcing each insulated separate conductor to bend into the section of its respective configured opening. A switch lead frame of an electrical conductor is preferably formed to include proximal ends bent to conjugate with configured openings. Each proximal end may have an insulation displacement connector.

A resilient member may be centered on the switch lead frame as a moveable contact generally through the plane of the top from one stable position to another position upon application of force on the member and generally normal to the top. The member is preferably conductively associated with one of the insulation displacement connectors and extends distally from at least one proximal end. A contoured arm on the lead frame is most preferably distal of but conductive with another insulation displacement connector. The contoured arm may be positionable adjacent the resilient member beneath the top as an opposed contact. The contoured arm spaced from the resilient member in a normally switch open condition is preferably capable of momentary engagement by the resilient member when in a switch closed position.

The frangible area on each switch lead frame is between the member and the contoured arm. The frangible area may be arranged to carry together the resilient member and the contoured arm. A common terminal on the lead frame preferably juts distally from the members as a single connection. The common terminal may connect to an electrode of the electrosurgical handpiece. Several recesses in the top of the insulating switch base each may support and retain one switch lead frame with its member and contoured arm in position to be normally open a preset distance of switch travel but capable of engagement therebetween to complete conductive connection therethrough. A raised dimple on each contoured arm might preferably engage within the recesses and secure the position of the contoured arm relative to the member as a switch gap. A restriction in each recess may be near its respective configured opening for passage of each contoured arm. An interference channel may extend cantilevered from the edge of the insulating switch base near the configured openings to hold the cable relative to the configured openings. The interference channel may be dimensioned to squeeze the cable after insertion therein and might be a strain relief. An aperture is preferred in the surface of each insulation displacement connector. A slot on each insulation displacement connector preferably opens downwardly toward the bottom of the insulating switch base for receiving one insulated separate conductor. The slot is preferably of a width so as to move the insulation and make electrical connection between the insulation displacement connector and the conductive core of the insulated separate conductor.

A pair of cooperating barbs is preferably angled outwardly from each insulation displacement connector to secure within its configured opening upon installation after aligning each insulation displacement connector with its configured opening and seating the switch lead frame within its recess and severing the frangible area. Passages may be positioned in the insulating switch base beneath the frangible areas to cooperate and permit severing. An insulating membrane is most preferably attached from edge to edge over the seated switch lead frame positioned within the recesses of the insulating switch base. A molded encasement is preferably applied to the bottom and edges of the insulating switch base and over portions of the membrane near the edges leaving at least the membrane over the member unencased.

A method of assembling a switch having a plurality of contacts in an automated process includes providing a cable having a plurality of individually insulated separate electrical conductors. It is preferred that the method has the step of having an insulating switch base prepared of a dielectric material and with configured openings to receive at least one of the insulated separate conductors. The step of driving the insulated separate conductors into the configured openings to locate and support the insulated separate conductors within the insulating switch base after forcing each insulated separate conductor to bend into a section of its respective configured opening is preferably included. The method may include the step of pressing the cable near the insulated separate conductors into an interference channel on the insulating switch base which channel acts as a strain relief. The step of forming a switch lead frame to include at least one pair of opposed contacts carried together as a unit and having at least two insulation displacement connectors may also be included. The further step of locating recesses in the top of the insulating switch base to support and retain switch lead frame opposed contacts in position to be normally open but capable of completing electrically conductive connection therebetween may be a part of the method. Installing the switch lead frame on the insulating switch base by aligning the insulation displacement connectors with configured openings and the opposed contacts with the recesses is another preferred step.

The method may include the step of guiding the insulation displacement connectors into the configured openings for perpendicular communication with each insulated separate conductors. The step of seating the switch lead frame into the insulating switch base for conjugating the insulation displacement connectors within the configured openings and setting the gap between the opposed contacts within the recesses is preferred. The step of displacing the insulation on the insulated separate conductors with the respective insulation displacement connector while at substantially the same time separating the plurality of contacts by severing interconnecting frangible areas of the switch lead frame is another part of the method.

The method may have the added step of separating conjoined switch lead frames is performed while severing the frangible areas. The method may also include the added step of attaching an insulating membrane over the seated switch lead frame and insulating switch base. The method might have the added step of trimming excess insulated separate conductors to prevent protrusion from the insulating switch base. The method may include the added step of encasing the assembled switch having a plurality of contacts in an insulator.

A tool for the assembly of an insulating switch base and a switch lead frame may preferably include a support to position and retain the insulating switch base bottom in alignment to receive the switch lead frame. An inserter for forcing each separate insulated conductor into its respective configured opening causing the separate insulated conductors to bend into a section of its respective configured opening might be provided. The inserter may have a holder proximal of the insulating switch base for application of controlled force to the separate insulated conductors during insertion. A translating carrier preferably locates the switch lead frame relative to and in alignment with recesses through the insulating switch base top.

A moveable tool stationed over the translating carrier is preferably able to engage selective portions of the switch lead frame for controlled movement thereof toward the recesses. The moveable tool may include lugs for engaging apertures on the insulation displacement connectors to drive each insulation displacement connectors into its configured opening and chisels for severing frangible areas when applied over and then into passages on the insulating switch base. The moveable tool most preferably has preset protrubrances for engaging and setting the contoured arms upon the seating of the switch lead frame within the insulating switch base so that a raised dimple is engaged with the recess to set the gap of the switch.

DETAILED DESCRIPTION OF THE INVENTION

Figure 1:
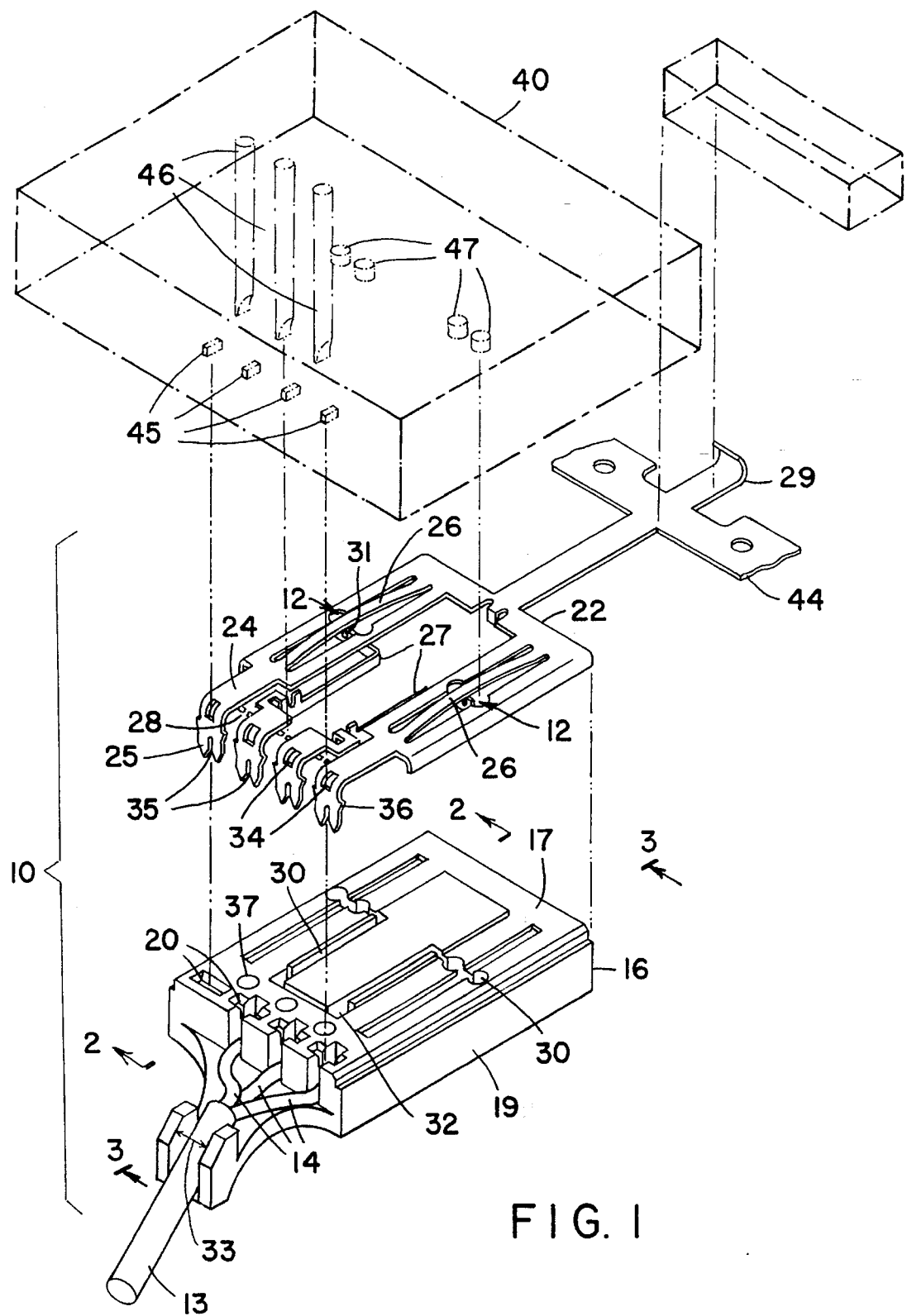
FIG. 1 is an exploded view of the tool and switch in perspective to illustrate the assembly method and the interaction of the tool and switch lead frame and insulating base.

A switch 10 for an electrosurgical handpiece 11 has a plurality of contacts 12 and a cable 13 having a plurality of individually insulated separate electrical conductors 14 each with a conductive core 15 surrounded by a dielectric. An insulating switch base 16 of a dielectric material is generally planar in shape. The insulating switch base 16 includes a top 17 and bottom 18 and an edge 19 surrounding thereabout. Configured openings 20 extend at least through the top 17 of the insulating switch base 16 and at least one edge 19 thereof. The configured openings 20 are each ready to receive at least one of the insulated separate conductors 14.

Figure 2:
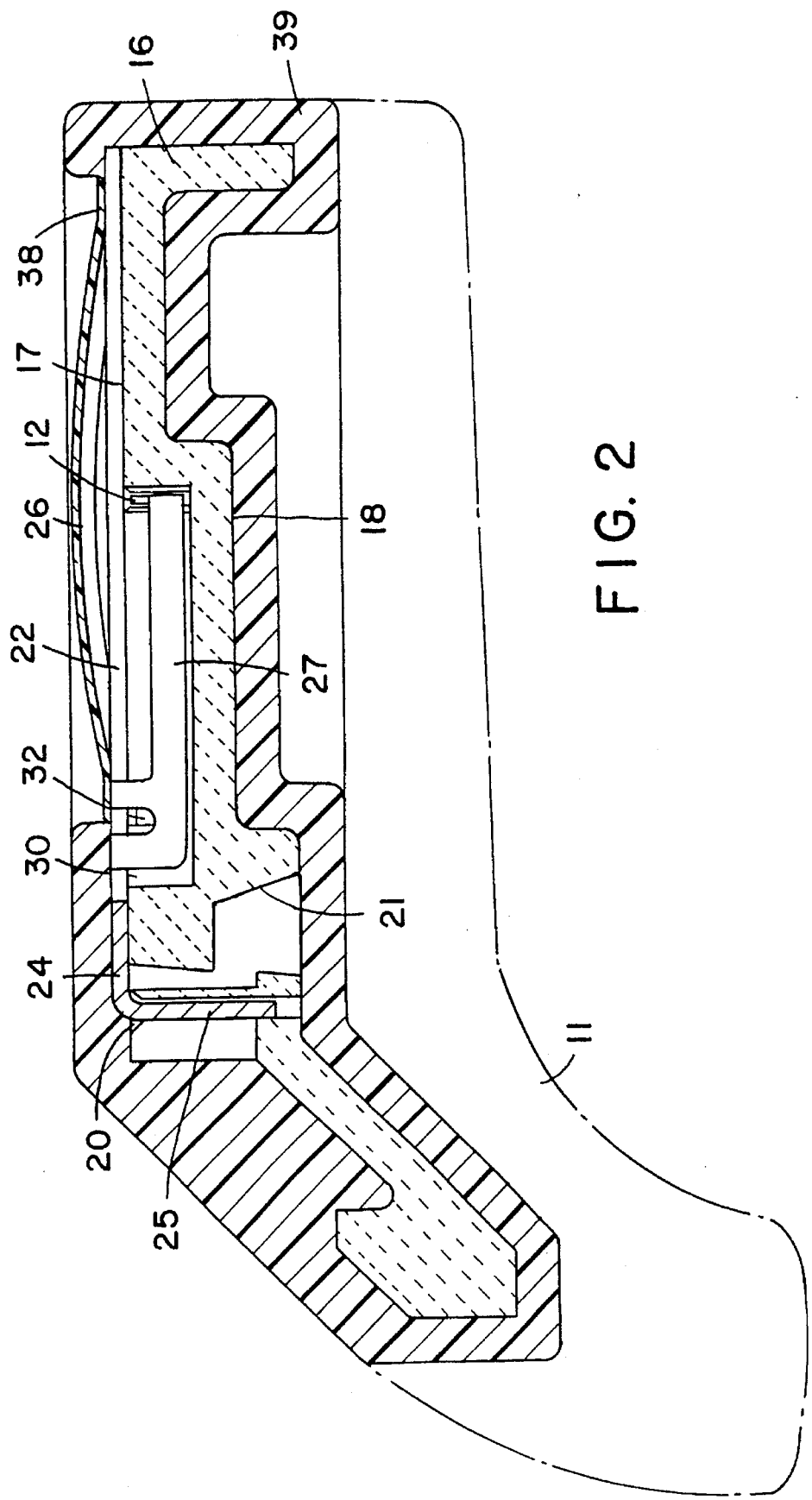
FIG. 2 is an side view in cross section of the fully assembled switch with its over molded encasement as would be seen along line 2—2 in FIG. 1.

A section 21, see FIG. 2, is located within each configured opening 20. The section 21 provides a barrier that redirects, by bending the conductor during insertion and after contact, each insulated separate conductor 14 from its respective configured opening 20 towards the bottom 18, thus locating and supporting the insulated separate conductor 14 within the insulating switch base 16. Each proximal end 24 has an insulation displacement connector 25. The switch lead frame 22 can be used in a progressive operation of any conductive metal by stamping but is preferably beryllium copper.

A resilient member 26 in the form of a leaf spring is centered on the switch lead frame 22 as a moveable contact 12 generally through the plane of the top 17 from one stable position to another position upon application of force on the member 26 directed generally normal to the top 17. The member 26 is conductively associated with one of the insulation displacement connectors 25 and extends distally from at least one proximal end 24. A contoured arm 27 on the lead frame 22 is distal of but conductive with another insulation displacement connector 25. The contoured arm 27 is positionable adjacent the resilient member 26 beneath the top 17 with its opposed contact 12. The contoured arm 27 is spaced from the resilient member 26 in a normally switch open condition and is capable of momentary engagement by the resilient member 26 when in its switch closed position.

Figure 3:
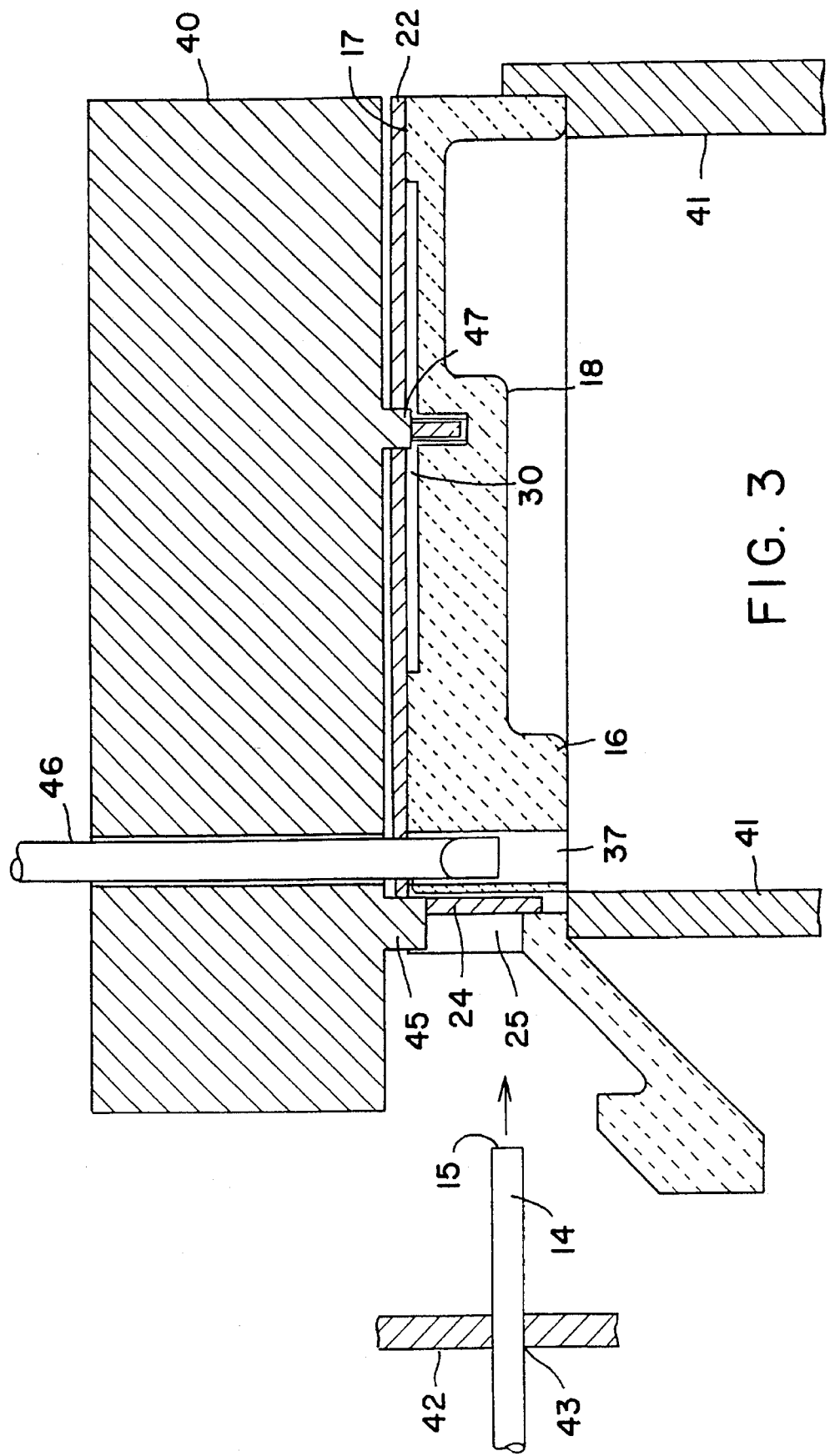
FIG. 3 is a partial side view in cross section of the switch as assembled and as seen along line 3—3 of FIG. 1.
Figure 4:
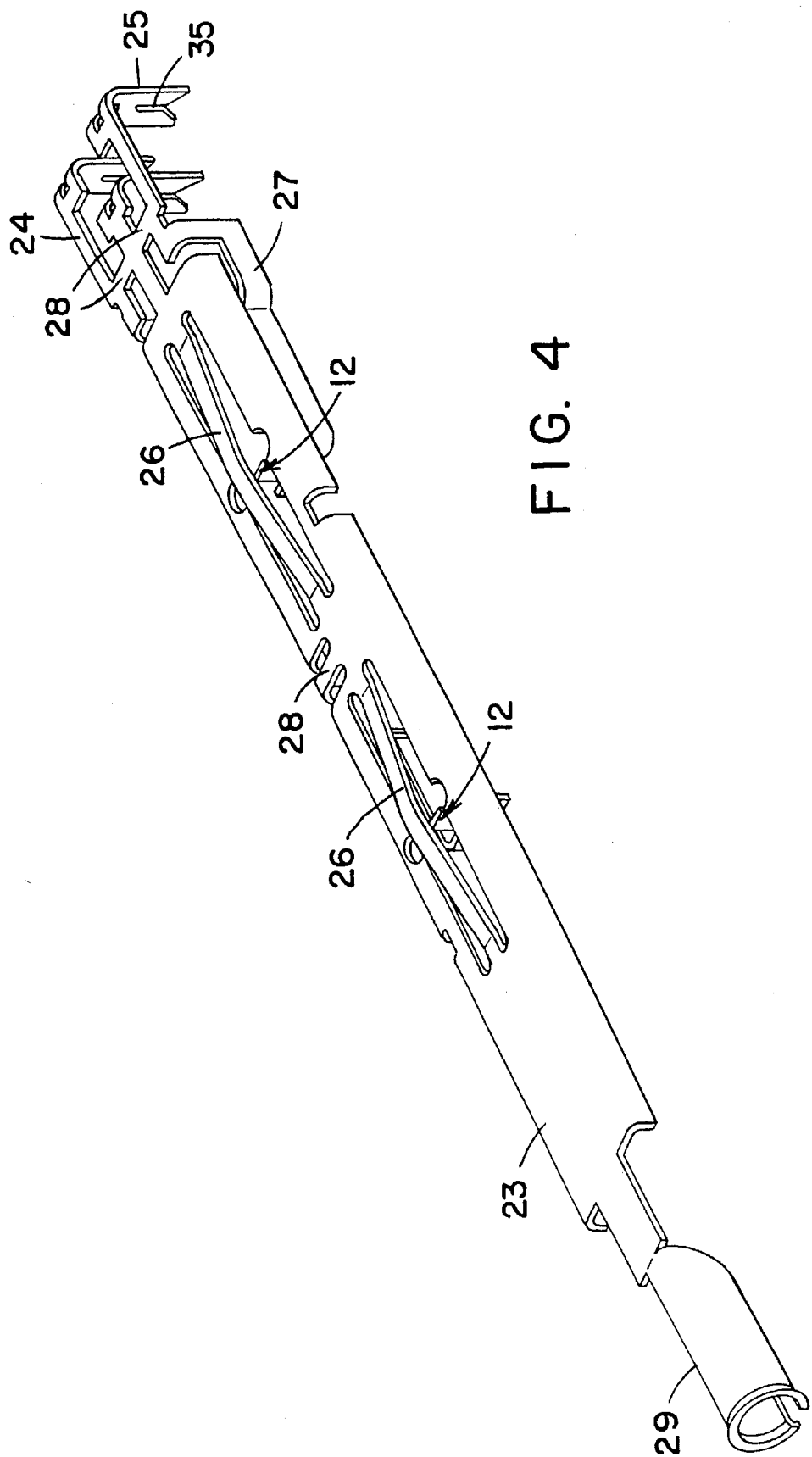
FIG. 4 is a perspective view of an alternate version of the switch lead frame wherein there is a plurality of contacts set in line as opposed to side by side which is the arrangement of FIG. 1.

A frangible area 28 on each switch lead frame 22 is between the member 26 and the contoured arm 27. The frangible area 28 is arranged to carry together the resilient member 26 and the contoured arm 27. A common terminal 29 on the lead frame 22 juts distally from the members 26 as a single connection. The common terminal 29 connects to an electrode (not shown) of the electrosurgical handpiece 11. Several recesses 30 in the top 17 of the insulating switch base 16 each support and retain one switch lead frame 22 with its member 26 and contoured arm 27 in position to be normally open a preset distance of switch travel but capable of engagement therebetween to complete conductive connection therethrough. As shown in FIGS. 2 and 3 the recess 30 extends from the top 17 towards the bottom 18 and parallel to the edge 19 see FIG. 1, thereby allowing space for the resilient member 26 to generally travel through the plane of the top 17. A raised dimple 31 on each contoured arm 27 engages within its recess 30 and secures the position of the contoured arm 27 relative to the member 26 as a switch gap. A restriction 32 in FIGS. 1 and 2 in each recess 30 is near its respective configured opening 20 for passage of each contoured arm 27. An interference channel 33 extends cantilevered from the edge 19 of the insulating switch base 16 near the configured openings 20 to hold the cable 13 relative to the configured openings 20. The interference channel 33 is dimensioned to squeeze the cable 13 after insertion therein and is a strain relief. An aperture 34 is in the surface of each insulation displacement connector 25. A slot 35 on each insulation displacement connector 25 in FIG. 1 opens downwardly toward the bottom 18 of the insulating switch base 16 for receiving one insulated separate conductor 14. The slot 35 is of a width so as to move the insulation and make electrical connection between the insulation displacement connector 25 and the conductive core 15 of the insulated separate conductor 14.

A pair of cooperating barbs 36 is angled outwardly from each insulation displacement connector 25 to secure within its configured opening 20 upon installation after aligning each insulation displacement connector 25 with its configured opening 20 and seating the switch lead frame 22 within the recesses 30 and severing the frangible area 28. Passages 37 positioned in the insulating switch base 16 beneath the frangible areas 28 cooperate to permit severing. An insulating membrane 38 in FIG. 2 is attached from edge 19 to edge 19 over the seated switch lead frame 22 positioned within the recesses 30 of the insulating switch base 16. A molded encasement 39 is applied to the bottom 18 and edges 19 of the insulating switch base 16 and over portions of the membrane 38 near the edges 19 leaving at least the membrane 38 over the member 26 unencased.

A method of assembling a switch 10 having a plurality of contacts 12 in an automated process includes providing a cable 13 having a plurality of individually insulated separate electrical conductors 14. The method has the step of having an insulating switch base 16 prepared of a dielectric material and with configured openings 20 to receive at least one of the insulated separate conductors 14. The step of driving the insulated separate conductors 14 into the configured openings 20 to locate and support the insulated separate conductors 14 within the insulating switch base 16 after forcing each insulated separate conductor 14 to bend into a section 21 of its respective configured opening 20 is included. The method includes the step of pressing the cable 13 near the insulated separate conductors 14 into an interference channel 33 on the insulating switch base 16 which channel 33 acts as a strain relief. The step of forming a switch lead frame 22 to include at least one pair of opposed contacts 12 carried together as a unit and having at least two insulation displacement connectors 25 is included. The further step of locating recesses 30 in the top 17 of the insulating switch base 16 to support and retain switch lead frame 22 opposed contacts 12 in position to be normally open but capable of completing electrically conductive connection therebetween is a part of the method. Installing the switch lead frame 22 on the insulating switch base 16 by aligning the insulation displacement connectors 25 with configured openings 20 and the opposed contacts 12 with the recesses 30 is another step.

The method has the step of guiding the insulation displacement connectors 25 into the configured openings 20 for perpendicular communication with each insulated separate conductors 14. The step of seating the switch lead frame 22 into the insulating switch base 16 for conjugating the insulation displacement connectors 25 within the configured openings 20 and setting the gap between the opposed contacts 12 within the recesses 30 is followed. The step of displacing the insulation on the insulated separate conductors 14 with the respective insulation displacement connector 25 while at substantially the same time separating the plurality of contacts 12 by severing interconnecting frangible areas 28 of the switch lead frame 22 is another part of the method.

The method has the added step of separating conjoined switch lead frames 22 is preformed while severing the frangible areas 28. The method includes the added step of attaching an insulating membrane 38 over the seated switch lead frame 22 and insulating switch base 16. The method has the added step of trimming excess insulated separate conductors 14 to prevent protrusion from the insulating switch base 16. The method includes the added step of encasing the assembled switch 10 having a plurality of contacts 12 in an insulator.

A moveable tool 40 for the assembly of an insulating switch base 16 and a switch lead frame 22 includes a support 41 to position and retain the insulating switch base 16 bottom 18 in alignment to receive the switch lead frame 22. An inserter 42 for forcing each separate insulated conductor 14 in FIG. 3 into its respective configured opening 20 causing the separate insulated conductors 14 to bend into a section 21 of its respective configured opening 20 is provided. The inserter 42 has a holder 43 proximal of the insulating switch base 16 for application of controlled force to the separate insulated conductors 14 during insertion. A translating carrier 44 locates the switch lead frame 22 relative to and in alignment with recesses 30 in the insulating switch base top 17.

Moveable tool 40 in FIG. 1, stationed over the translating carrier 43, is able to engage selective frangible areas 28 of the switch lead frame 22 for controlled movement thereof toward the passages 37. The moveable tool 40 includes lugs 45 for engaging apertures 34 on the insulation displacement connectors 25 to drive each insulation displacement connector 25 into its configured opening 20 and chisels 46 for severing frangible areas 28 when applied over and then into passages 37 on the insulating switch base 16. The moveable tool 40 has preset protrubrances 47 for engaging and setting the contoured arms 27 upon the seating of the switch lead frame 22 within the insulating switch base 16 so that the raised dimple 31 is engaged with the recess 30 to set the gap of the switch 10.

As used herein and throughout the term distal and variations thereof means near the patient and conversely the term proximal and variations thereof means away from the patient, i.e. toward the operating site. Similarly, the terms top and bottom as used in this disclosure are merely with respect to the orientation shown throughout the figures. It should be appreciated that the selection of top and bottom although the proper terms for the anticipated orientation of the switch during its typical usage are not limiting but are merely for purposes of description of the relative relationship of the preferred embodiment. Skilled artisans will no doubt understand how the invention can be practiced in many different way once the disclosure herein is appreciated.

What is claimed is:

1. A switch with a plurality of contacts comprising:

a cable having a plurality of individually insulated separate electrical conductors each with a conductive core surrounded by a dielectric;

an insulating switch base of a dielectric material and generally planar in shape, the insulating switch base with a top and bottom larger than an edge surrounding thereabout;

configured openings extending at least through the top of the insulating switch base and at least one edge thereof, the configured openings each ready to receive at least one of the insulated separate conductors;

a section within each configured opening located to redirect, by bending the conductor during insertion and after contact, each insulated separate conductor from its respective configured opening towards the bottom to locate and support the insulated separate conductors within the insulating switch base;

a switch lead frame of an electrical conductor formed to include proximal ends bent to conjugate with configured openings, each proximal end having an insulation displacement connector;

a resilient member centered on the switch lead frame as a moveable contact generally through the plane of the top from one stable position to another position upon application of force on the resilient member and generally normal to the top, the resilient member conductively associated with one of the insulation displacement connectors and extending distally from at least one proximal end;

a contoured arm on the lead frame and distal of but conductive with another insulation displacement connector, the contoured arm positionable adjacent the resilient member beneath the top as an opposed contact, the contoured arm spaced from the resilient member in a normally switch open condition but capable of momentary engagement by the resilient member when in a switch closed position;

several recesses in the top of the insulating switch base each formed to support and retain the switch lead frame with its resilient member and contoured arm in position to be normally open a preset distance of switch travel but capable of engagement therebetween to complete conductive connection therethrough;

a slot on each insulation displacement connector, each slot open downwardly toward the bottom of the insulating switch base for receiving one insulated separate conductor, the slot of a width so as to move the insulation and make electrical connection between the insulation displacement connector and the conductive core of the insulated separate conductor, and a pair of cooperating barbs angled outwardly from each insulation displacement connector to secure within its configured opening upon installation after aligning each insulation displacement connector with its configured opening and seating the switch lead frame within the recesses.

2. The switch of claim 1 wherein each insulation displacement connector includes an aperture in the surface thereof.

3. The switch of claim 1 wherein an interference channel extends cantilevered from the edge of the insulating switch base near the configured openings to hold the cable relative to the configured openings, the interference channel dimensioned to squeeze the cable after insertion therein and be a strain relief.

4. The switch of claim 1 wherein a common terminal on the lead frame juts distally from the resilient member as a single connection.

5. The switch of claim 4 wherein the common terminal is connected to an electrode of an electrosurgical handpiece.

6. The switch of claim 1 wherein an insulating membrane is attached from edge to edge over the switch lead frame positioned within the recesses of the insulating switch base.

7. The switch of claim 6 wherein a molded encasement is applied to the bottom and edge of the insulating switch base and over portions of the membrane near the edges leaving at least the membrane over the resilient member unencased.

8. The switch of claim 1 wherein the contoured arm has a raised dimple to engage within the recesses and secure the position of the contoured arm relative to the resilient member as a switch gap.

9. The switch of claim 1 wherein each recess near its respective configured opening includes a restriction through which the contoured arm passes.

10. A switch for an electrosurgical handpiece, the switch having a plurality of contacts comprising:

a cable having a plurality of individually insulated separate electrical conductors each with a conductive core surrounded by a dielectric;

an insulating switch base of a dielectric material and generally planar in shape, the insulating switch base with a top and bottom larger than an edge surrounding thereabout;

configured openings extending at least through the top of the insulating switch base and at least one edge thereof, the configured openings each ready to receive at least one of the insulated separate conductors;

a section within each configured opening located to redirect, by bending the conductor during insertion and after contact, each insulated separate conductor from its respective configured opening towards the bottom to locate and support the insulated separate conductors within the insulating switch base;

a switch lead frame of an electrical conductor formed to include proximal ends bent to conjugate with configured openings, each proximal end having an insulation displacement connector;

a resilient member centered on the switch lead frame as a moveable contact generally through the plane of the top from one stable position to another position upon application of force on the resilient member and generally normal to the top, the resilient member conductively associated with one of the insulation displacement connectors and extending dismally from at least one proximal end;

a contoured arm on the lead frame and distal of but conductive with another insulation displacement connector, the contoured arm positionable adjacent the resilient member beneath the top as an opposed contact, the contoured arm spaced from the resilient member in a normally switch open condition but capable of momentary engagement by the resilient member when in a switch closed position;

a common terminal on the lead frame juts distally from the resilient member as a single connection, the common terminal connects to an electrode of the electrosurgical handpiece;

several recesses in the top of the insulating switch base each formed to support and retain the switch lead frame with its resilient member and the contoured arm in position to be normally open a preset distance of switch travel but capable of engagement therebetween to complete conductive connection therethrough;

a raised dimple on the contoured arm to engage within its recess to secure the position of the contoured arm relative to the resilient member as a switch gap;

a restriction in each recess near its respective configured opening for passage of the contoured arm;

an interference channel extends cantilevered from the edge of the insulating switch base near the configured openings to hold the cable relative to the configured openings, the interference channel dimensioned to squeeze the cable after insertion therein and be a strain relief;

an aperture in the surface of each insulation displacement connector;

a slot on each insulation displacement connector, each slot open downwardly toward the bottom of the insulating switch base for receiving one insulated separate conductor, the slot of a width so as to move the insulation and make electrical connection between the insulation displacement connector and the conductive core of the insulates separate conductor;

a pair of cooperating barbs angled outwardly from each insulation displacement connector to secure within its configured opening upon installation after aligning each insulation displacement connector with its configured opening and seating the switch lead frame within the recesses;

passages positioned in the insulating switch base;

an insulating membrane is attached from edge to edge over the switch lead frame positioned within the recesses of the insulating switch base, and a molded encasement is applied to the bottom and edges of the insulating switch base and over portions of the membrane near the edges leaving at least the membrane over the resilient member unencased.

* * * * *